(12) United States Patent
Friedman (10) Patent No.: US 6,312,254 B1
(45) Date of Patent: Nov. 6, 2001

(54) DISPENSER FOR HEATING AND EXTRUDING DENTAL MATERIAL

(76) Inventor: Joshua Friedman, P.O. Box 2867, Danbury, CT (US) 06813

( * ) Notice: Subject to any disclaimer, the term of this patent is extended or adjusted under 35 U.S.C. 154(b) by 0 days.

(21) Appl. No.: 09/667,851

(22) Filed: Sep. 22, 2000

(51) Int. Cl.[7] ............................. A61C 3/00; A61C 19/00
(52) U.S. Cl. ................................. 433/32; 433/90
(58) Field of Search ................. 433/32, 80, 89, 433/90; 222/146.5

(56) References Cited

U.S. PATENT DOCUMENTS

| | | | |
|---|---|---|---|
| 3,831,815 | * 8/1974 | Glasgow | 222/94 |
| 3,951,308 | * 4/1976 | Thirtle | 222/39 |
| 4,065,034 | * 12/1977 | Callan | 222/391 X |
| 4,330,280 | 5/1982 | Dougherty | 433/90 |
| 4,384,852 | 5/1983 | Welsh | 433/90 |
| 4,472,141 | 9/1984 | Dragan | 433/90 |
| 4,974,752 | * 12/1990 | Sirek | 222/146.5 |
| 5,061,179 | 10/1991 | Dragan | 433/90 |
| 5,125,836 | 6/1992 | Dragan | 433/90 |
| 5,236,269 | * 8/1993 | Handy | 401/1 |
| 5,306,147 | 4/1994 | Dragan | 433/90 |
| 5,489,207 | 2/1996 | Dragan | 433/90 |

* cited by examiner

*Primary Examiner*—Nicholas D. Lucchesi (57) ABSTRACT

A dispenser for controllably heating a compule of dental material removably inserted in the dispenser and for extruding dental material from the compule. The dispenser includes an elongated tubular barrel having a substantially semi-cylindrical front end to accommodate the body of the compule, a cavity at the front end of the dispenser open to the atmosphere and a slot disposed transverse to the longitudinal axis of the for accommodating an end flange of the compule when the compule is inserted into the dispenser. The dispenser further includes a housing having one end connected to the tubular barrel and an opposite end having an extended handle in the form of a pistol grip, a plunger reciprocally mounted in the tubular barrel having a piston extending in alignment with the longitudinal axis of the cavity and a manually movable lever arm coupled to the plunger by means of a rack and pinion mechanism to dispense dental material from from the dispenser. The lever and handle are adapted to be held in one hand for manually controlling the movement of the plunger relative to said handle. The dispenser further includes a heating unit disposed in the cavity at the front end of the dispenser for heating the compule, a battery supply, and an electrical control unit connected to the battery supply for controlling the supply of electrical energy to the heating unit, with visual indicators for indicating temperature and battery level conditions.

15 Claims, 6 Drawing Sheets

DISPENSER FOR HEATING AND EXTRUDING DENTAL MATERIAL

FIELD OF THE INVENTION

This invention relates to a dispenser for heating dental material in a compule and for controllably extruding the heated dental material from the dispenser prior to clinical application.

BACKGROUND OF INVENTION

In applicants co-pending patent application Ser. No. 09/020,107, the disclosure of which is herein incorporated by reference, a method is disclosed for preheating dental composite material within a container before extruding the material from the container into an oral cavity for clinical application. The dental composite material is preheated to an elevated temperature above that of ambient temperature just prior to placement into a prepared tooth in the oral cavity. The prepared tooth is then clinically treated by exposure to light radiation while the dental restorative composite material is at the elevated temperature. Conversely, at present, photocurable dental materials are extruded into the patients mouth at ambient temperature from a standard dispensing device and cured by exposure to light radiation at ambient temperature.

In accordance with the findings of the applicant and as taught in the aforementioned patent the physical properties of photocurable dental material(s) are enhanced when preheated just prior to clinical usage. Examples of dental materials which can be enhanced by preheating prior to use include restorative materials (commonly referred to as filling materials), etching agents, bleaching compositions, dental cements, impression materials and more particularly photocurable dental restorative materials.

Applicants co-pending application also teaches preheating one or more standard pre-filled compules of dental material using a small heating device capable of housing a plurality of pre-filled compules in a removable section of the device. The removable section acts as a heat sink for all of the compules permitting the removable section to be removed after being heated to an elevated temperature and placed close to the patient, preferably upon a standard bracket tray which most dentists presently use to hold instruments and medicaments, during a given operative procedure. Prior to use a heated compule is placed in a conventional dispenser by the dentist and dental material is then extruded directly into the prepared dental cavity.

Conventional dispensers are mechanical extruding devices such as taught by U.S. Pat. No. 4,384,853 to Welsh and U.S. Pat. No. 5,489,207 to Dragan and have no other purpose. The dispenser of the present invention is a hand held portable device designed to heat a compule of dental material which is removably inserted in the dispenser to an elevated temperature above that of ambient and to controllably extrude the pre-heated dental material from the compule directly from the dispenser into an oral cavity for clinical application.

SUMMARY OF THE INVENTION

The present invention is directed to a dispenser for controllably heating a compule of dental material which is removably inserted into the dispenser and for extruding dental material from the compule. The compule has a circumferential flange at one end which surrounds a movable sealing plug and has a generally cylindrical body in which the dental material to be extruded is stored. The dispenser of the present invention comprises:

an elongated section having a front end with a cavity open to the atmosphere for removably receiving said compule and a rear end, a housing connected to the rear end of said elongated section with a handle in the form of a pistol grip extending from said housing, a plunger mounted for reciprocal movement in the rear end of said elongated section with said plunger having a piston extending from one end of said plunger in alignment with the cavity, a manually movable lever arm having one end connected to said plunger for controllably advancing the piston into engagement with said compule to dispense dental material from the dispenser, said movable lever being spaced apart from said handle so that said lever and handle may be held in one hand by the operator of the dispenser and squeezed for controllably advancing the plunger as the lever moves relative to said handle, the movable lever arm is preferably connected to the plunger by means of a rack and pinion mechanism.

a source of electrical power, a heating unit in juxtaposition to said cavity at said front end of said dispenser for heating the compule when in said cavity with said heating unit including a heating element; and an electrical control unit connected in said housing to said source of electrical power for controlling the supply of electrical energy to said heating element in the heating unit. The use of a rack and pinion mechanism provides this design the ability to control the force and the rate of dispensing by varying the measurements of the rack and pinion dimensions.

BRIEF DESCRIPTION OF THE DRAWINGS

The features and advantages of the dispenser of the invention will become apparent from the following detailed description when read in conjunction with the accompanying drawings of which.

DETAILED DESCRIPTION OF THE PREFERRED EMBODIMENT

Referring to the drawings, and more particularly to FIGS. 1–4, there is shown a manual dispenser 10 for heating dental material stored in a disposable compule 12 and for controllably extruding the dental material from the compule 12. The disposable compule 12 is removably mounted in a compule holder 13 formed at the front end of the dispenser 10. The compule 12 may be any standard size commercially available cartridge in which dental material 14 is stored. The compule 12 is removably inserted into the dispenser 10 and may be manually ejected from the dispenser 10 for replacement after the photocurable dental material 14 has been emptied from the compule 12 as will be more fully discussed hereafter. A standard compule 12, as is presently commercially available, has a generally cylindrically shaped body 11 with an outer circumferential flange 9 at the rear end thereof with a diameter larger than the diameter of the body 11 and a nozzle tip 15 at its forward end having a discharge orifice 16 through which the dental material is discharged. The nozzle tip 15 may lie at any desired angle relative to the body 11. A movable sealing plug 17 holds the dental material 14 secure in the body 11 of the compule 12.

The dispenser 10 comprises a tubular barrel 18 having a semi-cylindrical shaped open front end 19 and a cavity 21 forming, in combination, a compule holder 13 into which the compule 12 is removably inserted. The tubular barrel 18 has a bore 20 extending longitudinally therethrough in coaxial alignment with a cavity 21 at the front end 19 of the dispenser 10. The cavity 21 is dimensioned to accommodate the generally cylindrical body 11 of the compule 12. A slot 22 is formed in the walls 23 of the open front end 19 of the dispenser 10 lying transverse to the longitudinal axis of the cavity 21 abutting the tubular barrel 18. The slot 22 is dimensioned to accommodate the flanged end 9 of the compule 12.

Figure 1:
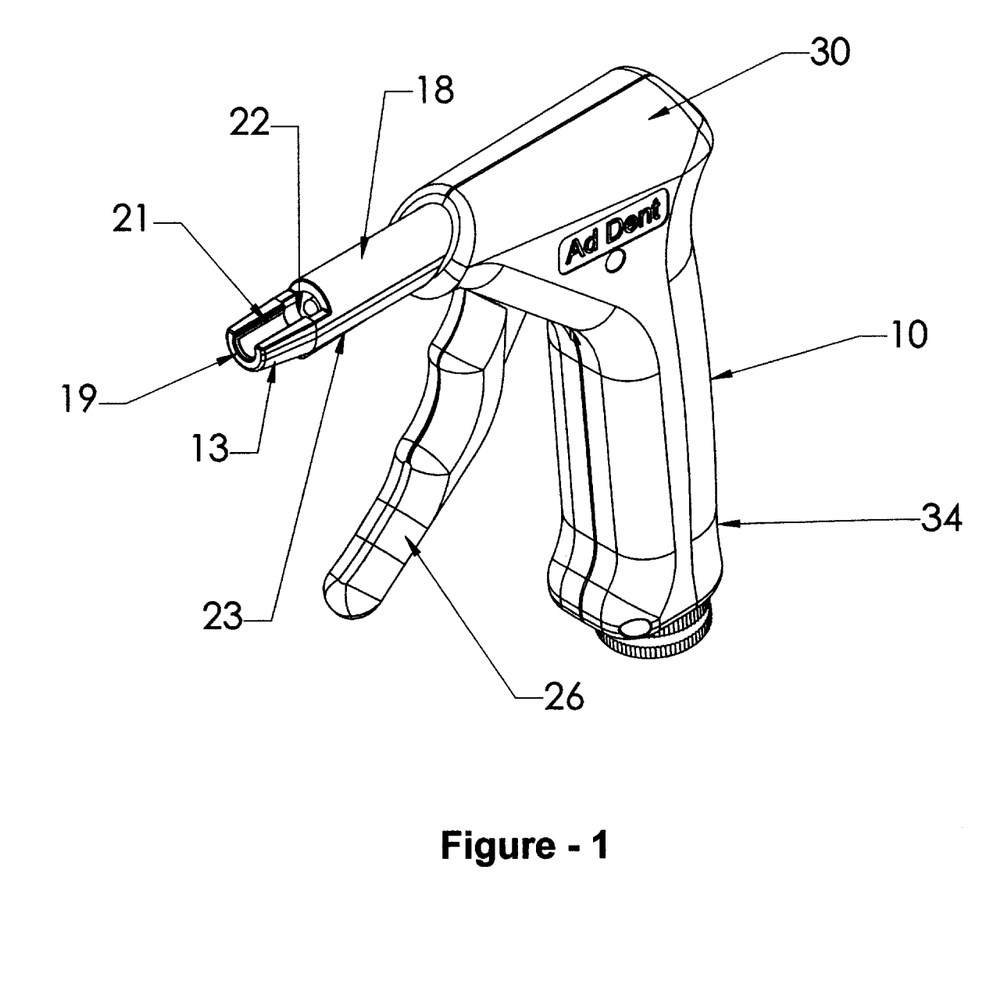
FIG. 1 is a perspective view of the manually operated dispenser of the present invention.
Figure 2:
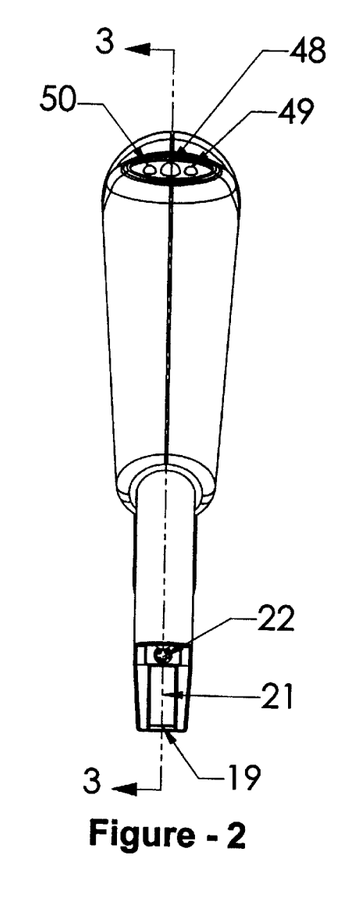
FIG. 2 is a top view of the dispenser shown in FIG. 1.
Figure 3:
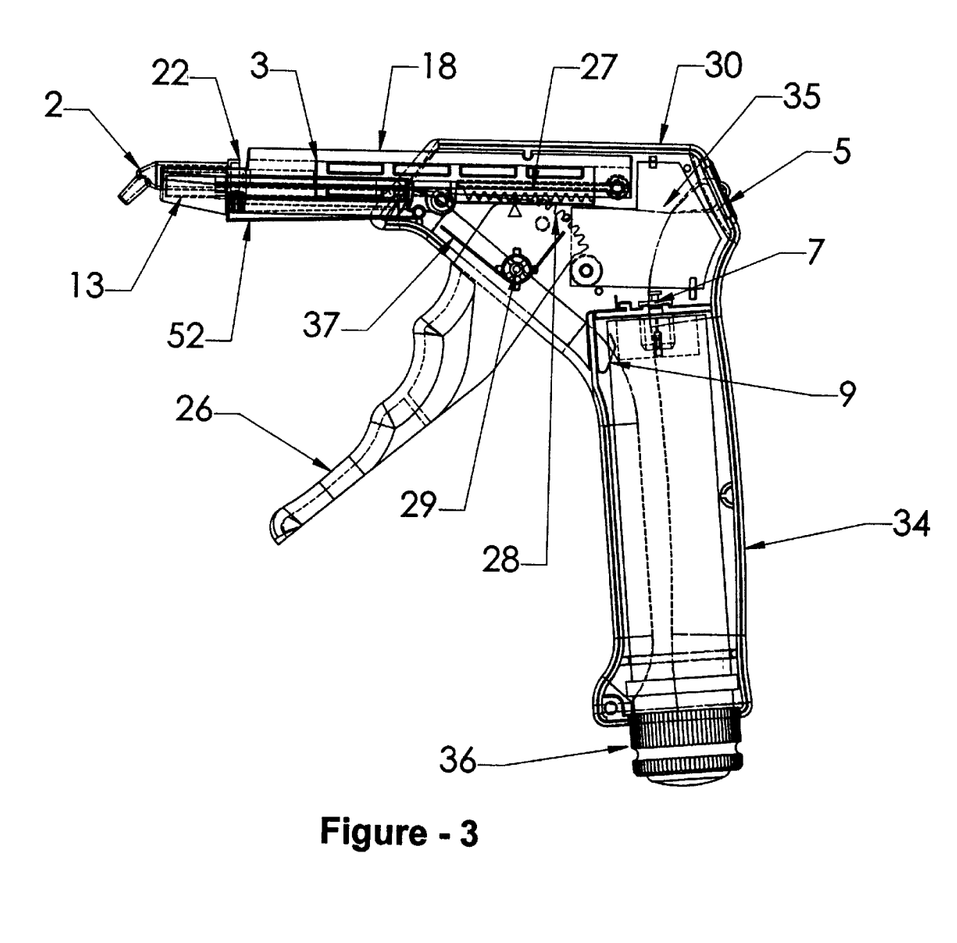
FIG. 3 is a side elevation of the manually operated dispenser of the present invention taken along the lines 3—3 of FIG. 2.

A plunger 24 is controllably reciprocated within the bore 20 of the tubular barrel 18 by means of a direct drive gear coupling 25 between the plunger 24 and a manually movable lever arm 26 in a configuration commonly referred to as a rack and pinion drive mechanism. The direct drive gear coupling 25 includes a rack represented by a first set of gear teeth 27 substantially at the rear end of the plunger 24 interconnected to a pinion represented by a second set of gear teeth 28 formed at one end of the manually movable lever arm 26. The manually movable lever arm 26 is pivotally connected though a pivot pin 29 secured to the casing 30 of the dispenser 10 which partially surrounds the barrel 18 as shown in FIG. 1. The plunger 24 has a piston 32 at the forward end thereof, as more clearly shown in FIG. 4, which is in coaxial alignment with the longitudinal axis of the cavity 21 and in alignment with the sealing plug 17 of the compule 12 when the compule 12 is inserted into the dispenser 10. The piston 32 moves the movable sealing plug 17 within the compule 12 as the plunger 24 is advanced by manually squeezing the lever arm 26.

Figure 6:
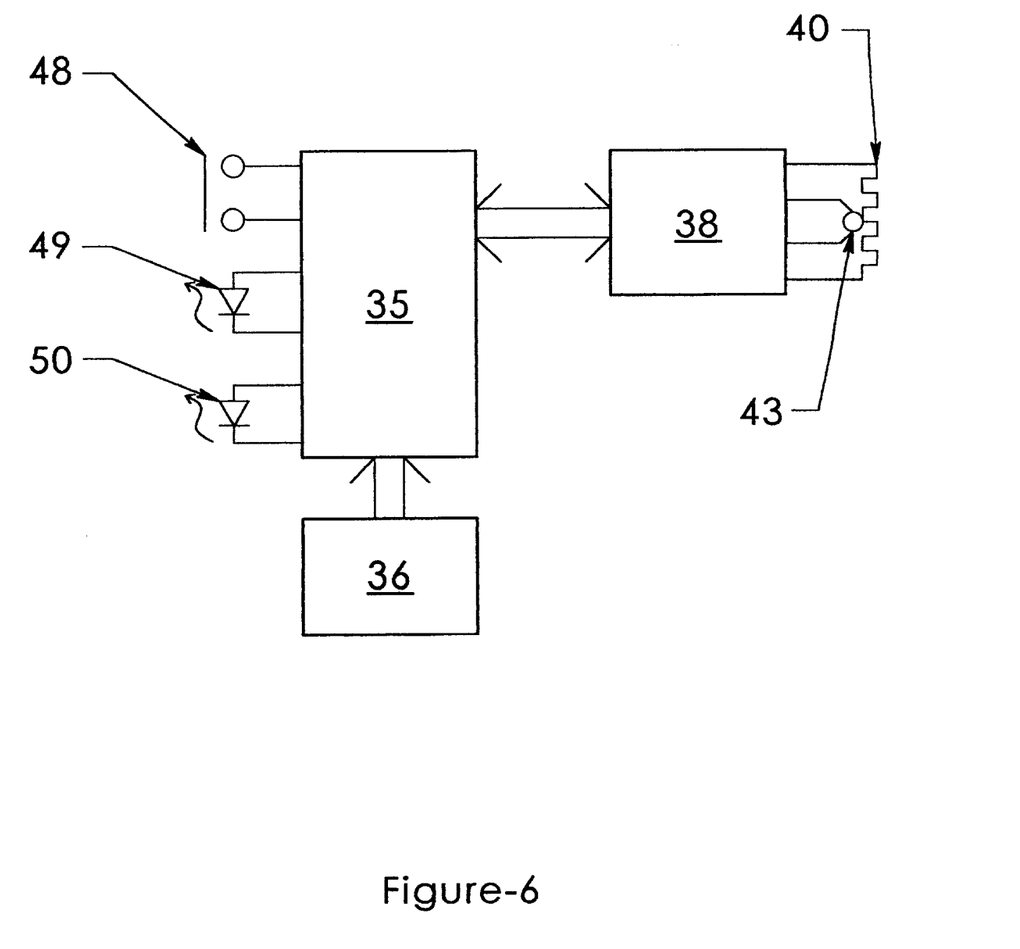
FIG. 6 is a block diagram of the heating control unit for controlling the temperature of the heating unit in FIG. 5.

The tubular barrel 18 is connected to a housing 30 containing an electrical control unit 35 which is shown in block diagram in FIG. 6. The housing 30 has a hollow tubular section 34 forming a handle for the dispenser 10 in the shape of a pistol grip. A battery or battery pack 36 which functions as a source of electrical power for heating the compule 12 is stored in the tubular section 34. The tubular section 34 of the housing 30 and the lever arm 26 are normally spaced apart such that the lever arm 26 and tubular section 34 can be conveniently held in one hand by an operator of the dispenser 10 and squeezed to move the lever arm 26 relative to the tubular section 34. A coiled tension spring 37 is connected to the movable lever arm 26 and to the housing 30 to maintain the lever arm 26 in a normally retracted position spaced apart from the tubular section 34 until the lever arm 26 is squeezed. Upon release of the movable lever arm 26 the coiled tension spring 37 forces the lever arm 26 back to its normal retracted position. In operation, the operator squeezes the movable lever arm 26 relative to the tubular section 34 which causes the plunger 24 to move forwardly pushing the piston 32 against the sealing plug 17 which, in turn, discharges dental material 14 from the dispenser 10. The amount of dental material 14 being discharged is proportional to the applied squeezing force on the movable lever arm 26. Once the operator releases the grip on the movable lever arm 26 the coiled tension spring 36 moves the movable lever arm 26 away from the tubular section 34 retracting the plunger 24. In the normal or unsqueezed position the plunger 24 is fully retracted and the lever arm 26 is spaced apart from the tubular section 34.

Figures 5, 5A:
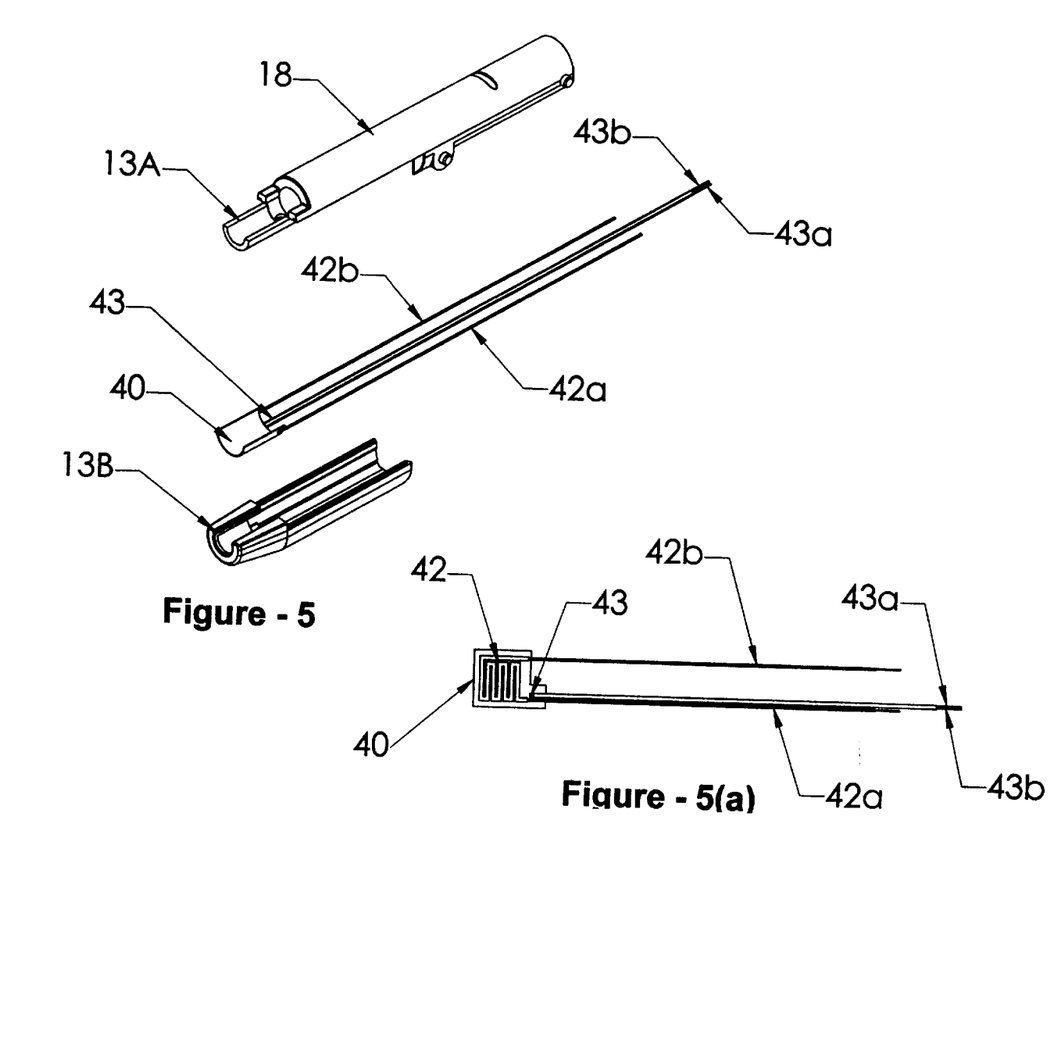
FIG. 5 is an exploded elevational view of a preferred embodiment for the front end of the dispenser shown in FIGS. 2 and 3.
FIG. 5(a) is a view of the interior of the heating unit showing the heating element and thermocouple.

A preferred embodiment of the front end of the dispenser 10 is shown in elevation in FIGS. 5 and 5(*a*) wherein the compule 12 has a first compule holder portion 13A extending from the tubular barrel 18 and a second compule holder portion 13B into which the first compule holder portion 13A slides after insertion of a heating unit 40 for raising the temperature of the compule 12 when mounted in the compule holder 13. The heating unit 40 is in the form of a flexible sheet of material which can be flexed into a desired shape to form a liner which covers the internal surface of the cavity 21 of the compule holder 13 into which the compule 12 is mounted. The heating unit 40 may be secured between the first compule holder portion 13A and the second compule holder portion 13B by means of an adhesive or any other conventional means. Alternatively, the heating unit 40 may be lined over the cavity 21 of the compule holder 13 or molded into the compule holder 13 to form an integral component thereof. The heating unit 40 includes a heating element 42 of a highly conductive material composed preferably of a metal such as copper, nichrome, aluminum or graphite in the form of a wire strip embedded in a plastic covering such as polyester. In addition the heating unit 40 includes a temperature sensor such as a conventional type J thermocouple 43. The wire strip heating element 42 is arranged in a pattern having a serpentine or interlaced geometry as shown in FIG. 5(*a*) and as disclosed in applicants co-pending patent application Ser. No. 09/020,107 the disclosure of which is herein incorporated by reference. The opposite ends of the wire strip heating element 42 in the heating unit 40 is connected to a set of electrical wires 42*a* and 42*b* which extend from the heating unit 40 through slots in the bore 20 of the tubular barrel 18 to the control unit 35 in a series circuit relationship. The thermocouple 43 in the heating unit 40 senses the temperature of the heating element 42 directly in the compule holder 13. Two wires 43*a* and 43*b* extend from the thermocouple 43 as shown in FIG. 5(*a*) which also extend from the heating unit 40 through slots in the bore 20 of the tubular barrel 18 to a heater drive 38 shown in FIG. 6.

The control unit 35, which preferably consists of a microprocessor (not shown), operates in conjunction with a source of electrical power such as the battery or battery pack 36 and the heater drive 38 to form a control system as shown in the block diagram of FIG. 6 for regulating the temperature of the heating element 42 in the heating unit 40. The battery pack 36 may consist of a group of rechargeable cells with any voltage between from 2.5 to 12 volts, preferably 3.6 volts and a capacity of at least 1.0 Ah. The battery pack 36 is the sole power source for the dispenser.

The heater drive can be turned on and off by the control unit 35 so that the unit can go into a low-power mode when it is not in use. When the heater drive 38 is turned on, the battery voltage is applied to the heater. As the temperature rises, the type J thermocouple voltage rises. When the heater assembly temperature reaches its set point, the heater 38 drive is disabled. If the temperature drops below the set point, the heater drive will be enabled for a period of time necessary to reach the set point. The set point is controlled by a potentiometer.

The control unit 35 also provides an operator interface and operates all control functions. The operator interface consists of one pushbutton 48 and two LED's 49 and 50. The pushbutton power switch 48 will turn the dispenser on and off. The LED power indicator 49 will light when power is on and will blink when the battery pack voltage drops below 3.0V (in the case of a 3.6 volt battery). The LED 50 is a temperature indicator which will light when the desired temperature is reached. Pressing the power button 48 activates the control unit 35 which turns on the power LED 49 and heats up the heating unit 40. When the heating unit 40 attains the desired temperature the heater drive 38 will send a signal to the to the Control unit 35 which is programmed to wait 2 seconds and turn on the LED 50. The temperature of the heating unit 40 will continue to be regulated for a programmed period of 5 minutes unless during the 5 minute interval the power button 48 is again depressed. Depressing the power button 48 a second time, i.e., after it is turned on deactivates the control unit 35. The control unit 35 will also disable the supply of electrical power to the heating unit 40, when the microprocessor detects a low battery condition (e.g. a battery voltage of <3.0 volts) and cause the power LED 49 to blink during that time.

Figure 4:
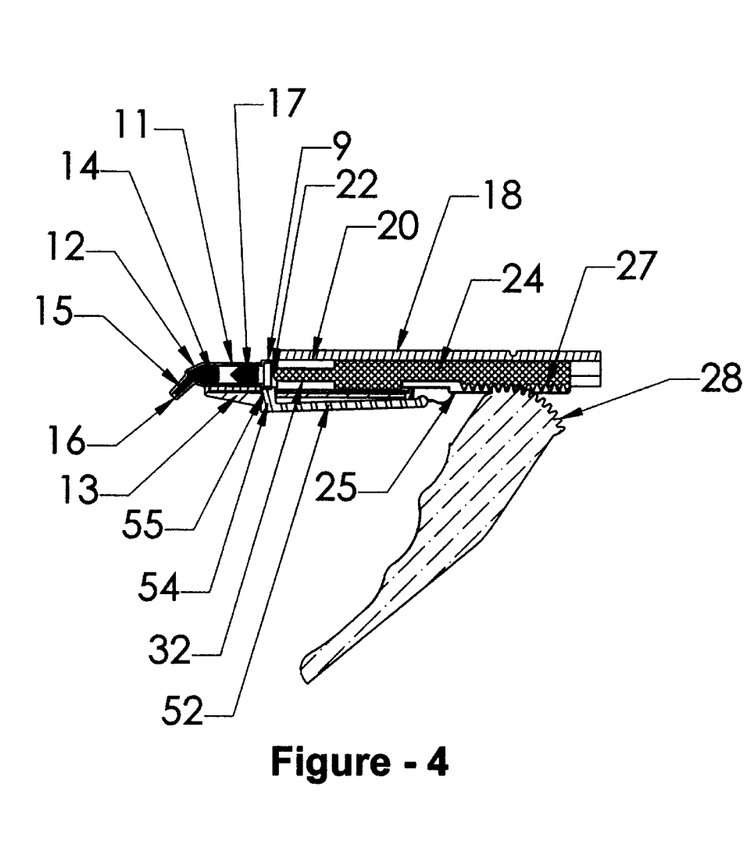
FIG. 4 is an enlarged cross sectional schematic of the front end of the dispenser, the plunger in the dispenser and the interconnected gearing for controlling the extrusion of dental material in accordance with the present invention.
Figure 4A:
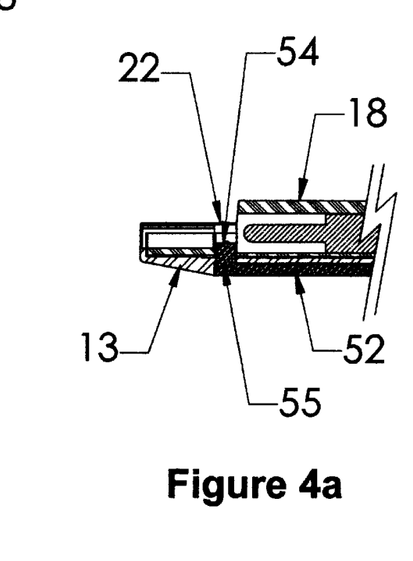
FIG. 4(a) is an enlarged fragmentary view in cross section of the front end of the dispenser of FIG. 4.

The compule holder 13 at the front end 19 of the dispenser 10 has an ejector mechanism 51 including a compule ejector arm 52 which is pivotally connected to the tubular body 18 and extends into the compule holder 13 to permit the operator to quickly and easily remove the compule 12 from the compule holder 13. The ejector arm 52 has a head 54 extending into the slot 22 through an opening 55 in the underside of the compule holder 13 adjacent the flanged end 9 of the compule 12. The ejector arm 52 lies at an inclined angle relative to the longitudinal axis of the bore 20 in the tubular body 18 to provide additional mechanical advantage for moving the compule ejector arm 52. As shown in FIG. 4(*a*) when the compule 12 is to be removed from the compule holder 13 the ejector arm 52 is manually depressed causing the head 54 to push the flanged end 9 of the compule 12 upwardly out from the slot 22. In this position the operator can readily grip the compule 12 and remove it for replacement. With no compule 12 in place the ejector arm 52 remains flush with the body 18. The replacement of the compule 12 in the compule holder 13 repositions the ejector arm 52 as more clearly shown in FIG. 4.

What is claimed is:

1. A dispenser for heating and extruding dental material from a compule of dental material removably inserted within said dispenser comprising:

an elongated section having a front end with a cavity open to the atmosphere for removably receiving said compule and a rear end, a housing connected to the rear end of said elongated section with a handle in the form of a pistol grip extending from said housing, a plunger mounted for reciprocal movement in said elongated section with said plunger having a piston extending from one end of said plunger in alignment with the cavity, a manually movable lever arm having one end connected to said plunger for controllably advancing the piston into engagement with said compule to dispense dental material from the dispenser, said movable lever being spaced apart from said handle so that said lever and handle may be held in one hand by the operator of the dispenser and squeezed for controllably advancing the plunger as the lever moves relative to said handle, a source of electrical power, a heating unit in juxtaposition to said cavity at said front end of said dispenser for heating substantially the entire compule when placed in said cavity such that all or substantially all of the material in the compule is heated at one time with said heating unit including a heating element; and an electrical control unit connected in said housing to said source of electrical power for controlling the supply of electrical energy to said heating element in the heating unit.

2. A dispenser for heating and extruding dental material as defined in claim 1 wherein said source of electrical power is a battery or battery pack which is removably located in said housing.

3. A dispenser for heating and extruding dental material as defined in claim 2 wherein said heating unit is in the form of a flexible sheet liner covering an internal surface of the cavity in contact with the compule.

4. A dispenser for heating and extruding dental material as defined in claim 3 wherein said heating element is a resistive wire.

5. A dispenser for heating and extruding dental material as defined in claim 4 wherein said heating unit further includes a thermocouple.

6. A dispenser for heating and extruding dental material as defined in claim 1 further comprising a manually movable compule ejector arm having a head extending through an opening in the dispenser below said cavity for manually ejecting said compule upon manually depressing the ejector arm to lift the head thereby raising the compule upwardly out from the cavity.

7. A dispenser for heating and extruding dental material from a compule removably inserted within the dispenser with the compule having a circumferential flange at one end thereof surrounding a movable sealing plug and a generally cylindrical body in which the dental material to be extruded is stored, said dispenser comprising:

an elongated tubular barrel having a substantially semi-cylindrical front end with said front end having a cavity open to the atmosphere with dimensions to accommodate the generally cylindrical body of said compule and a slot disposed transverse to the longitudinal axis of said cavity between the cavity and the tubular barrel for accommodating the circumferential flange of said compule, a housing having one end connected to said tubular barrel and having a handle in the form of a pistol grip extending from said tubular barrel, a plunger reciprocally mounted in said tubular barrel with said plunger having a piston extending from one end of said plunger in alignment with the longitudinal axis of said cavity adjacent the movable sealing plug in said compule, a manually movable lever arm having one end connected to said plunger for controllably advancing the piston into engagement with said sealing plug to dispense said dental material from the dispenser, said movable lever being spaced apart from said handle so that said lever and handle may be held in one hand by the operator of the dispenser and squeezed for controllably advancing the plunger as the lever moves relative to said handle, a heating unit disposed in the cavity at said front end of said dispenser for heating the body of said compule;

a battery supply, and an electrical control unit connected to said battery supply for controlling the supply of electrical energy to said heating unit.

8. A dispenser as defined in claim 7 further comprising a coiled spring connecting said movable arm to said housing to position the movable arm toward a normally retracted position spaced apart from said handle such that when the movable lever arm is squeezed relative to the handle and released by the operator it will return to said normally retracted position.

9. A dispenser as defined in claim 8 further comprising a gear coupling for interconnecting said plunger to said manually movable lever arm.

10. A dispenser as defined in claim 9 wherein said gear coupling comprises a rack and pinion.

11. A dispenser as defined in claim 10 wherein said gear coupling is adjustable by varying the dimensions of said rack and pinion for changing the force and rate of dispensing of said dental material from the dispenser to adapt the dispenser to different viscosity dental materials.

12. A dispenser as defined in claim 7 further comprising a manually movable compule ejector arm having a head extending through an opening in the dispenser below said cavity in alignment with said slot for manually ejecting said compule upon manually depressing the ejector arm thereby raising the compule upwardly from the slot.

13. A dispenser as defined in claim 1 further comprising a rack and pinion gear coupling for interconnecting said plunger to said manually movable lever arm with the dimensions of said rack and pinion being adjustable for changing the force and rate of dispensing of said dental material from the dispenser to adapt the dispenser to different viscosity dental materials.

14. A dispenser for heating and extruding dental material from a compule of dental material removably inserted within said dispenser, with the compule having a nozzle through which the material is discharged, said dispenser comprising:

an elongated section having a front end and a rear end with said front end having a cavity adapted for the removable placement of said compule, a plunger mounted for reciprocal movement within the elongated section of said dispenser, said plunger having a piston extending from one end of said plunger in alignment with the cavity, means connected to said plunger to advance the piston into engagement with said compule in response to the operator of the dispenser for controllably dispensing dental material from the dispenser, a heating unit having a heating element located in the front end of said dispenser for heating substantially the entire compute in said cavity such that all or substantially all of the material in the compule is heated at one time;

a supply of electrical energy and means for controlling the supply of electrical energy to said heating element in the heating unit.

15. A dispenser as defined in claim 14 wherein said front end has an opening exposing said cavity to the atmosphere with the opening sized so that said compute can be manually placed in said cavity and with the dispenser further comprising a manually movable compule ejector arm having a head extending through another opening in the dispenser below said cavity for manually ejecting said compute upon manually depressing the ejector arm to lift the head thereby raising the compule upwardly out from the cavity.

* * * * *